United States Patent [19]

Moreau et al.

[11] Patent Number: 5,654,797

[45] Date of Patent: Aug. 5, 1997

[54] METHOD AND APPARATUS FOR MONITORING THE DIAMETER OF THERMALLY SPRAYED PARTICLES

[75] Inventors: Christian Moreau; Patrick Gougeon, both of Boucherville; Mario Lamontagne, Ville Lemoyne, all of Canada

[73] Assignee: National Research Council of Canada, Ottawa, Canada

[21] Appl. No.: 605,772

[22] Filed: Feb. 22, 1996

[51] Int. Cl.$^6$ ............................. G01N 15/02; G01N 21/00
[52] U.S. Cl. ................................................. 356/336; 356/338
[58] Field of Search ................................. 356/28, 45, 335, 356/336, 338

[56] References Cited

U.S. PATENT DOCUMENTS

| | | | |
|---|---|---|---|
| 3,680,961 | 8/1972 | Rudd | 356/102 |
| 4,411,519 | 10/1983 | Tagami | 356/45 |
| 4,441,816 | 4/1984 | Hencken et al. | 356/335 |
| 4,662,749 | 5/1987 | Hatton et al. | 356/336 |
| 4,854,705 | 8/1989 | Bachalo | 356/336 |
| 5,135,306 | 8/1992 | Kanebako et al. | 356/336 |
| 5,155,549 | 10/1992 | Dhadwal | 356/334 |
| 5,180,921 | 1/1993 | Moreau et al. | 250/554 |

OTHER PUBLICATIONS

Measurement of In-Flight Particle Parameters In Thermal Plasma Spraying Process By The Light Pulse Analysis Method; T. Sakuta et al; Jun. 1991; Proceedings of Japanese Symposium on Plasma Chemistry; pp. 175–180.

In-Flight Measurement of Particle Size and Temperature J. R. Fincke et al; 1988; pp. 367–370 (no month available).

On-Line Control of Plasma Spraying Process By Monitoring the Temperature, Velocity, and Trajectory of In-Flight Particles; C. Moreau et al, Jun. 1994, pp. 431 to 437.

Simultaneous Measurement of Particle Size, Velocity and Temperature; J R Fincke et al; Sep. 1992; pp. 559–565.

Laser Optical Diagnostics Complex For Investigation Of High-Temperature Heterogeneous Jets; S.M. Guselnikov et al; 1990; pp. 163–170 (no month available).

*Primary Examiner*—Frank G. Font
*Assistant Examiner*—Zandra V. Smith
*Attorney, Agent, or Firm*—Marks & Clerk

[57] ABSTRACT

In a method of monitoring in-flight particles, a mask in a is placed in a plane generally parallel to the direction of travel of the particles. The mask defines at least two slits that are generally parallel and lie in a direction having at least a component at right angles to the direction of travel. The slits have their ends offset relative to each other. The slits radiation emitted, scattered or absorbed by the particles is monitored as they traverse the slits field of view. The particles for which the radiation, emitted, scattered or absorbed which is collected through each slit as they sequentially traverse said slits bears a predetermined relationship are identified, and the size of the identified particles is determined from the amount of radiation emitted, scattered or absorbed as the identified particles traverse the slits.

22 Claims, 2 Drawing Sheets

METHOD AND APPARATUS FOR MONITORING THE DIAMETER OF THERMALLY SPRAYED PARTICLES

BACKGROUND OF THE INVENTION

1. Field of the Invention

This invention relates to an optical sensor for monitoring in-flight particles in thermal spray processes and other industrial processes.

Thermal spraying in general, and plasma spraying in particular, is a powerful technique widely used to produce protective coatings on a large variety of substrates. For example, thermal barrier coatings are plasma sprayed in producing aircraft engines and ceramic and metal coatings are thermally sprayed for various purposes.

The properties of coatings depend upon many spraying parameters, some of them being related to the spray gun operation. Consequently, spraying process control has been implemented by monitoring and regulating gun input variables. In plasma spraying, parameters such as arc current and power, arc gas flow rates, powder feed rate, and powder carrier gas pressure are controlled to keep them at predetermined optimum values. This control approach has been found to be complex because a large number of interrelated input variables must be monitored, and has been found to be incomplete because some variables, such as electrode wear state, cannot be monitored at all.

An alternative control approach is described in U.S. Pat. No. 5,180,921, in which the temperature and velocity of the sprayed particles are monitored before their impingement on the substrate. On-line measurement of these particle parameters, which directly influence the structure of the sprayed coatings, can provide an efficient feedback signal generator to perform feedback for the gun input parameters and a diagnostic tool to detect any problem during the coating operation.

Collecting information about particle flow is also useful in other industrial applications. For example, production of metallic powders by gas atomization involves the atomization of a molten metal by a series of gas jets and on-line measurement of the particle temperature, velocity and diameter provides key information about the state of the process.

2. Description of the Prior Art

Different techniques exist for measuring the diameter of in-flight particles in industrial environments. Some techniques are based on laser beam illumination of the in-flight particles to obtain particle characteristics. For example, dual beam laser Doppler anemometry has been proposed by M. J. Rudd (U.S. Pat. No. 3,680,961) and by R. Adrian and K. L. Orion in Applied Optics, 16 (1977) 677–684 to simultaneously measure the size and velocity of moving particles. D. J. Holve and K. D. Annen in Optical Engineering, 23 (1984) 591–603 described a different arrangement in which a laser beam is used to illuminate the moving particles and the scattered radiation is detected in the forward or backward direction. The particle size and velocity are obtained after deconvolution of the detected signals. To simplify the treatment of signals related to the shape of the laser beam, G. Grehan and G. Gouesbet, Applied Optics 25 (1986) 3527–3538, have developed a system for measuring the particle size and velocity using a top-hat beam technique. Measurement of the diameter and velocity of particles can also be obtained from the phase shift of the scattered laser radiation as described for example by W. D. Bachalo (U.S. Pat. No. 4,854,705), P. Buchhave, J. Knuhtsen and P. E. S. Olidag (U.S. Pat. No. 4,701,051) and T. A. Hatton and J. L. Plawsky (U.S. Pat. No. 4,662,749).

These prior art techniques give unreliable diameter measurements when the particles are not spherical, which is common in thermal spray processes when particles are not fully molten. Other approaches use more than one laser beam at different wavelengths and, from the intensity and/or polarization of the scattered radiation, the diameter and velocity of the moving particles are determined (for example, J. C. Wang and K. R. Henken in Applied Optics 25 (1986) 653–657, and U.S. Pat. No. 4,854,705 by W. D. Bachalo).

Different techniques have been used to measure particle parameters in thermal spray processes, including the particle temperature. Simultaneous measurement of particle size, velocity and temperature has been carried out by J. R. Fincke, W. D. Swank, C. L. Jeffery and C. A. Mancuso in Meas. Sci. Technol., 4 (1993) 559–565 in jets of plasma-sprayed particles. Particle size and velocity are obtained from a combination laser sizing system and laser Doppler velocimeter while the particle temperature is determined by two-color pyrometry. S. M. Guselnikov, A. G. Zavarzin, V. P. Lyagushkin, M. Mikhalchenko and O. P. Solonenko in Plasma Jets, Solonenko and Fedorchenko (EDS), VSP, 1990, p. 163–170 used a combination of the two-focus anemometry for velocity measurement, laser forward scattering technique for size measurement and two-color pyrometry for temperature measurement. In both cases, the optical arrangement is relatively complex and hardly usable in industrial environment.

Another approach has been described by J. R. Fincke, C. L. Jeffery and S. B. Englert in J. Phys. E: Sci. Instrum., 21 (1988) 367–370 in which the temperature and diameter of sprayed particles are measured using a laser beam. The temperature is obtained using the two-color pyrometry while the diameter is computed from the intensity of the scattered beam after deconvolution to take into account of the gaussian shape of the laser beam.

Two systems have been proposed to measure the particle size, velocity and temperature based on the detection of thermal radiation emitted by the hot incandescent sprayed particles passing through a volume of measurement of known dimensions. In both cases, the temperature is evaluated by two-color pyrometry and the velocity is computed from the time of flight of the particles in the volume of measurement.

In the approach developed by T. Sakuta, T Ohtsuchi, K. Sakai and T. Takashima, Proc. Jpn. Symp. Plasma Chem. 4 (1991) 175–180, the diameter is obtained from the rise time of the detected signals when the particles enter and exit the volume of measurement.

In the approach developed by K. R. Hencken, D. A. Tichenor and J. C. F. Wang (U.S. Pat. No. 4,441,816), particles are seen through a double-slit mask. The first slit is narrow in such a way that only a fraction of the section of the moving particle is seen by the detectors. The second slit is larger than the particle image so that the entire section of the particle is seen. The velocity is obtained from the transit time of the particles in this second slit while the diameter is computed from the ratio of the radiation intensities collected in each slit. Since the first slit must be narrower than the image of the smallest particle to be analyzed, the transit time in this slit becomes very short when particles are moving at high velocity requiring very fast photodetectors and acquisition electronics components. In both approaches, a laser beam must be focused at the center of the volume of measurement to trigger the acquisition electronics only when a particle is traveling in the focal plane of the collection optics.

An object of the invention is to alleviate the aforementioned problems.

SUMMARY OF THE INVENTION

According to the present invention there is provided a method of monitoring in-flight particles, comprising the steps of placing a mask in a plane generally parallel to the direction of travel of the particles, said mask defining at least two slits that are generally parallel and lie in a direction having at least a component at right angles to said direction of travel, and said slits further having their ends offset relative to each other; monitoring the radiation emitted, scattered or absorbed by said particles as they traverse said slits; identifying particles for which the radiation emitted, scattered or absorbed at each slit as they sequentially traverse said slits bears a predetermined relationship; and determining the size of the identified particles from the amount of said radiation emitted, scattered or absorbed as they traverse said slits.

Normally, the slits are of equal width and different lengths, in which case equal amounts of radiation are scattered, absorbed or emitted when an entire particle traverses both slits, and the size of the particles is determined when such equal amounts are detected. However, in theory the slits could have unequal widths so long as the relationship between them was known and this was taken into account in the calculations. They could also have equal lengths so long as their ends were offset.

Using the optical detection technique for measuring the temperature and velocity of in-flight particles has been described in U.S. Pat. No. 5,180,921, the particle velocity can be computed from the time of flight of the particles from the field of view of the first slit to the field of view of the second slit. The temperature can be measured using the two-color pyrometry technique. In this technique, the temperature of a radiating object is obtained, after calibration, from the ratio of light intensity detected at two different wavelengths.

The present invention thus describes a technique to measure not only the temperature and velocity of in-fight particles, but also their diameter, particularly in thermal spray processes and other industrial applications. The diameter measurement is carried out by using a modified two-slit mask whose geometry permits the localization of the particle in the field of view of the collection optics. Since the particle is entirely included in the volume of measurement, its diameter can be determined, after calibration, from the absolute intensity of the thermal radiation collected by the collection optics. Thus, for each particle analyzed, its temperature, velocity and diameter are measured simultaneously. Information about the state of the spray processes is obtained by on-line analysis of a representative sample of individual particles.

For particles at low temperature or in highly radiating environments, thermal radiation from the particles may be not intense enough to permit the detection and analysis of the particles. In that case, a light source can be used to illuminate the particles and the radiation scattered by the particles collected. From the analysis of detected signals, the diameter and velocity of the particles are measured.

The present invention thus provides a method and apparatus for monitoring simultaneously the temperature, velocity and diameter of the sprayed particles by detecting the thermal radiation emitted by hot in-flight particles.

In a preferred embodiment, the monitoring system consists of a sensor head located near the torch, an optical fiber and a detection box containing the photodetectors. A two-slit optical mask is placed on the tip of the optical fiber located in the sensor head. Only the light impinging on the two transparent slits engraved on the opaque mask can reach the optical fiber and thus be transmitted to the detection box.

The invention also provides an apparatus for monitoring in-flight particles, comprising a mask for location in a plane generally parallel to the direction of travel of the particles to be monitored, said mask defining at least two slits that are generally parallel, of different lengths, and lie in a direction having at least a component at right angles to said direction of travel, and said slits further having their ends offset relative to each other; detector means for monitoring the radiation emitted, scattered or absorbed by said particles as they traverse said slits; means for identifying particles that as they traverse each slit emit, scatter or absorb radiation according to a predetermined relationship; and processing means for calculating the size of the identified particles from the amount of said radiation emitted, scattered or absorbed by said particles.

BRIEF DESCRIPTION OF THE DRAWINGS

The invention will now be described in more detail, by way of example, only with reference to the accompanying drawings, in which.

DESCRIPTION OF THE PREFERRED EMBODIMENTS

The invention will be described with reference to an apparatus for measuring the size, temperature and velocities of particles emerging from a plasma spray gun.

Figure 1:
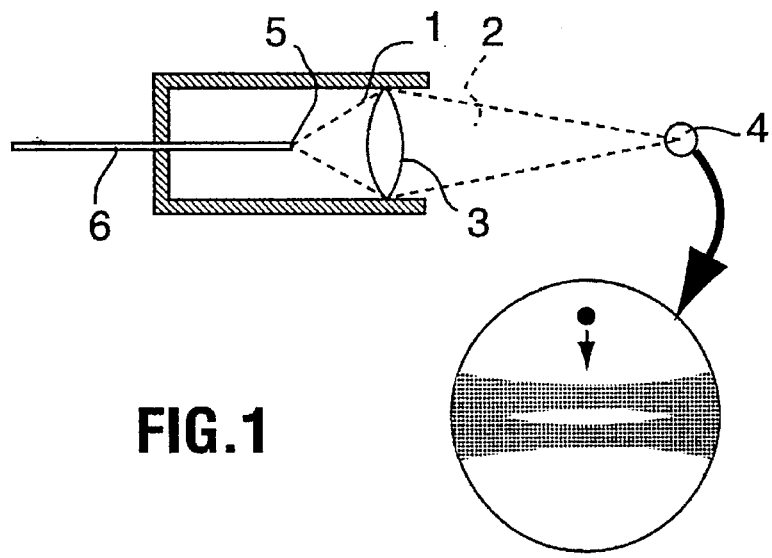
FIG. 1 is a diagram showing details of the sensor head of an apparatus in accordance with the invention.

As shown in FIG. 1, the apparatus has a sensor head 1 in the form of a cylindrical housing open at one end 2 for the entry of light and containing a lens 3 focusing an image of a particle 4 onto one end 5 of an optic fiber 6. The particle is assumed to be traveling along an axis in the plane of the paper and at right angles to the longitudinal axis of the sensor head 1.

Figure 2:
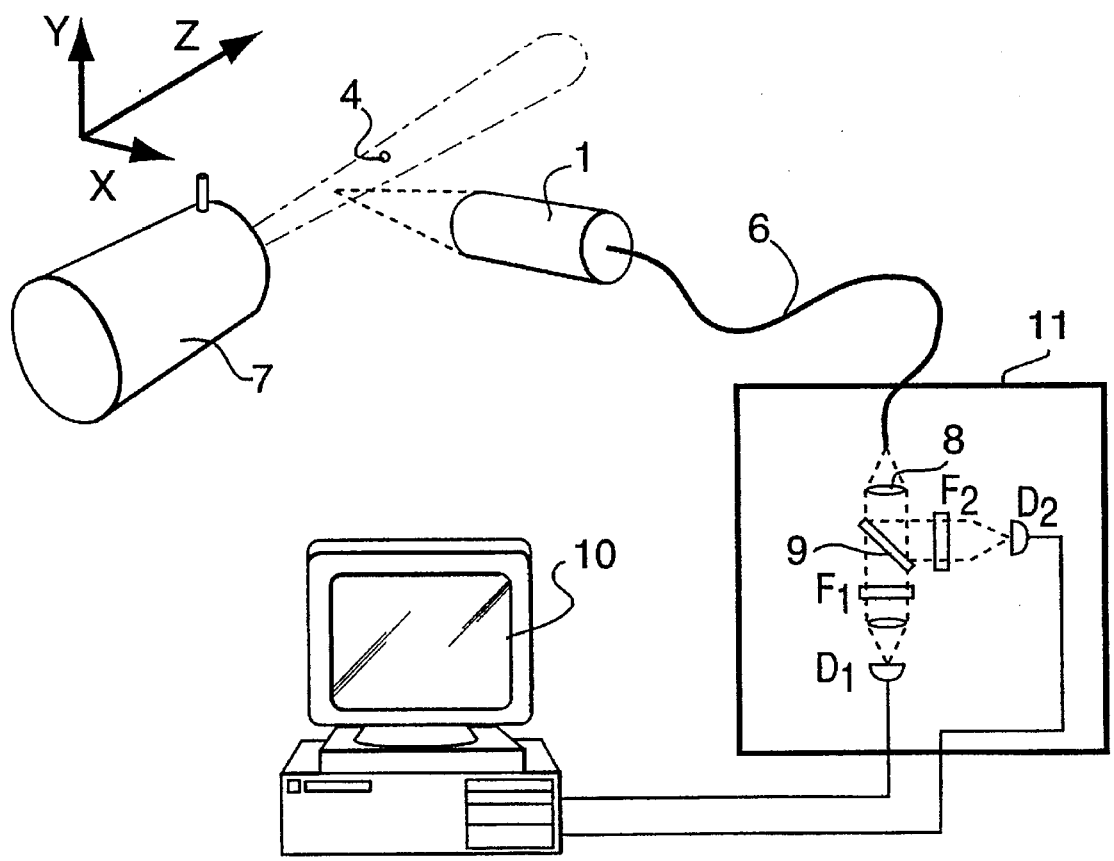
FIG. 2 is a general schematic diagram of the overall apparatus.

FIG. 2 shows plasma gun 7 directing particles along the z-axis past the sensor head 1.

The optic fiber 6 leads to a detection box 11 including a collimating lens 8 and a dichroic mirror 9, which splits the light into two beams, which are directed through bandpass filters $F_1$, $F_2$ respectively to detectors $D_1$, $D_2$. The outputs from the detectors are sent to the computer 10, which computes the particle size, temperature, and velocity.

The collected radiation is spectrally separated by a dichroic mirror and then filtered by the two bandpass filters $F_1$ and $F_2$. The wavelengths are selected in order to minimize the influence of the plasma radiation scattered by the particles. Signals from both detectors are amplified and fed to a rapid digitizing board in the computer 10. The digitized signals are analyzed by the personal computer, which computes the temperature, velocity and diameter of the in-flight particles.

Figure 3:
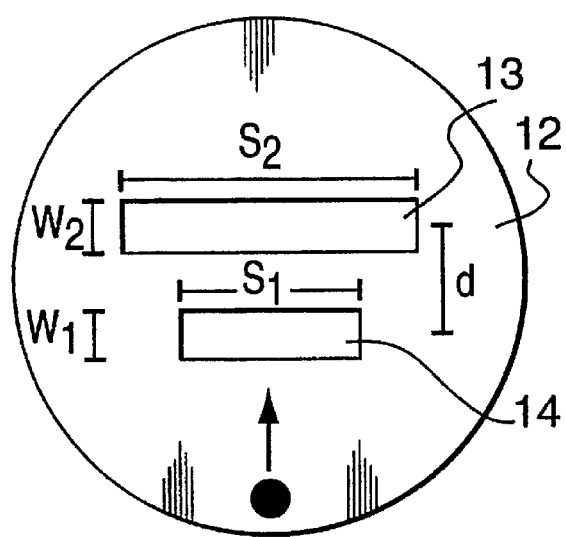
FIG. 3 is a detailed view of the slits.

As shown in more detail in FIG. 3, the end 5 of the optic fiber 6 in the sensor head 1 comprises an optical mask 12 with a pair of transparent slits 13, 14. The mask 13 is thus located on the tip of the optical fiber in the sensor head. As a particle 4 travels through the measurement volume, its image is seen twice by the detectors as its image moves from one slit to the second one (FIG. 3). The widths $w_1$ and $w_2$ of the slits are preferably 25 μm. Their lengths $S_1$ and $s_2$ are preferably 50 μm and 100 μm, respectively. The distance d between the slits is preferably 50 μm center-to-center. The magnification of the collection optics is preferably about 0.3. So the image of a 80 μm particle has a diameter of 24 μm in the plane of the optical mask 12. The width of the slits should be larger than the diameter of the image of the largest particles to be monitored.

The difference of the slit lengths $(S_2-S_1)$ should preferably exceed the diameter of the image of the largest particles to be monitored.

Figure 4:
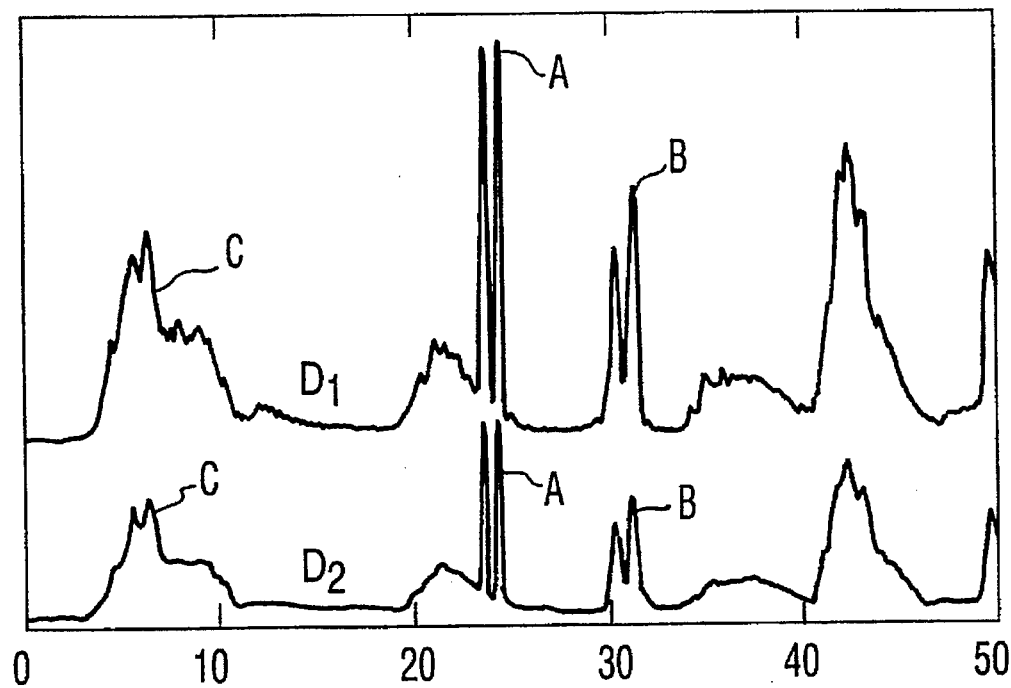
FIG. 4 is a chart showing signals output from the photodetectors.

When a particle 4 travels through the sensor field of view, its image is seen twice by the photodetectors as it moves from the first slit to the second. As a result, it generates a two-peak light pulse. FIG. 4 shows examples of signals collected by detectors $D_1$ and $D_2$ drawn as a function of time during the passage during the passage of a few particles in the sensor field of view. In FIG. 4, only two particles (corresponding to peaks A and B) were moving near the object plane (the plane conjugate to the slit plane) of the sensor head 1. Indeed, due to finite depth of field, only particles passing near the object plane can generate the characteristic two-peak signals. Particles out of this plane tend to generate broad merged peaks, such as C.

As described in the U.S. Pat. No. 5,180,921, for a particle moving within the depth of field of the collection optics, its temperature is measured by two-color pyrometry from the ratio of the radiation intensities collected by the two photodetectors. On the other hand, the particle velocity is calculated from the time elapsed between the two light pulses collected when the particle image moves from the first slit to the second. The distance between the two slits and the magnification of the detection optics being known, the particle velocity can be computed accordingly.

The particle diameter measurement disclosed in the present invention is based on the absolute radiation intensity detected at one wavelength (using detector $D_1$ or $D_2$). The surface of the particle, and thus its diameter, can be determined after calibration from the radiation intensity detected if the particle temperature is known. Indeed, from Planck's law the radiant power $P(\lambda, T)$ emitted from a surface S at a wavelength $\lambda$ is given by:

$$P(\lambda,T)d(\lambda) = \frac{c_1 S}{\lambda^5} \frac{\epsilon}{e^{c_2/\lambda T}-1} d(\lambda) \quad (1)$$

where $d(\lambda)$ is the wavelength range of detection centered on $\lambda$, $c_1$ and $c_2$ are universal radiation constants, $\epsilon$ is the emissivity and T the temperature of the radiating body. The signal detected at wavelength $\lambda$ can thus be written:

$$U(\lambda)=KP(\lambda,T)d(\lambda)=CS\epsilon f(T) \quad (2)$$

where K and C are constants that depend on the detection system and f(T) is a known function of temperature. So, from the signal detected with one detector, the surface of the radiating particle can be measured if it is entirely included in the sensor field of view.

The particular arrangement of the optical mask disclosed in the present invention is a simple and efficient means to determine if the particle is totally included in the sensor field of view. As shown in FIG. 3 the mask is composed of two slits 13, 14 of different length. The difference of length $(S_2-S_1)$ should be of the same order of magnitude as the diameter of the image of largest particles to be monitored. This difference can be larger to take into account any divergence in the trajectories of the moving particles in the vicinity of the sensor field of view. In this way, if the intensity of radiation detected through the first slit is equal to the one detected through the second slit, it follows that the entire image of the particle traveled through each slit. Thus, its surface area and diameter can be computed from the intensity of the collected radiation.

If the slit lengths are equal, the same fraction of the image could be seen by both slits and one cannot be sure that it was totally included in each of them.

As shown in FIG. 4, two particles crossed the sensor field of view near the object plane. The first one A, detected after 23 μsec, generated a two-peak pulse for which the intensity of each component was equal within a few percent. This indicates that the particle image was totally included in the slit area during its passage. For that particle, the computer 10 can thus calculate its temperature, velocity and diameter. The second particle B detected after about 30 μsec was not fully seen by the sensor head as the intensity of the second peak was significantly higher than the first.

According to Equation. 2, the emissivity of the particles must be taken into account to determine the particle size from the intensity of the detected signals. The emissivity at high temperature of many materials used in thermal spray processes is not known. In that case, the measured diameter must be considered as a relative value. This information is still very useful to determine the influence of the particle size on the temperature, velocity and trajectory (sizing effect) of the sprayed particles. If the emissivity is not known, absolute measurement of particle size can be carried out after calibration using particles of known dimensions.

The technique can be used also with particles at low temperature. In that case, the thermal radiation is not intense enough to be detected, and the in-flight particles must be illuminated with an intense light source. In this case, the radiation scattered by the particles is detected. The intensity of the light beam must be relatively uniform over the volume of measurement of the sensor head (about 350 μm×350 μm×3000 μm in the preferred embodiment). For each detected particle identified by the characteristic two-peak pulse whose intensities of the two peaks are equal, the relative diameter and velocity can be measured. The diameter measurement is possible since the intensity of the scattered radiation is proportional to the section of the particles. In this configuration, only one detector sensitive to the wavelength of the light source is required to perform the diameter and velocity measurement.

The main advantage of the technique disclosed in the present invention for monitoring thermally-sprayed particles over other techniques mentioned above is that it is simpler since it does not require any intense light sources or second detection assembly. This results in a more compact, rugged and easy-to-use sensor that does not require any special eye protection. The system requires only two photodetectors for the temperature, velocity and diameter measurements and avoids the use of coincidence electronic devices and the delicate alignment of a second detection assembly or light beam in the particle jet.

As mentioned above, two systems based on the detection of thermal radiation emitted by the hot particles have already been developed (Proc. Jpn. Symp. Plasma Chem. 4(1991) 175–180 and U.S. Pat. No. 4,441,816). Both systems require the use of a laser beam to localize the particle in the volume of measurement. The approach described in this last patent is based on the use of a mask with two slits of different widths. The width of the first slit must be narrower than the image diameter of the smallest particles. In thermal spray applications, typical particle size range from 10 to 80 μm. So, the size of this first slit should be smaller than 3 μm if an optical magnification of 0.3 is used. Since particle velocity in thermal spray processes can reach 500 m/sec and more the transit time of a particle in the field of view of the first slit is about 20 nsec. Thus the detectors and acquisition electronics must be very rapid to cope with such short-duration signals. The width of the slits required in the present invention is about 25 μm corresponding to transit times one order of magnitude longer, permitting to use less rapid optical and electronic components. The noise levels and costs of such components are lower.

While the slits $S_1$ and $S_2$ are described as having the same widths and different lengths, it is possible, although not preferred, to practice the invention width slits of the same length and different widths.

If the widths are different, the peaks will not be the same height when an entire particle is seen by both slits. However, the peaks will still bear a predetermined relationship to each other that depends on the difference in widths. The computer can be made responsive only to signals that conform to this relationship.

Similarly, the lengths can be the same as long as the slits are set in an overlapping relationship. For example, if the right end of slit $S_1$ were extended to the right of the right end of slit $S_2$ in FIG. 3, a particle moving partially over the end of slit $S_2$ would still pass over the entirety of the end of slit $S_1$, thereby giving rise to a difference in signals.

We claim:

1. A method of monitoring in-flight particles, comprising the steps of:
   a) placing a mask in a plane generally parallel to the direction of travel of the particles, said mask defining at least two slits that are generally parallel and lie in a direction having at least a component at right angles to said direction of travel, and said slits further having their ends laterally offset relative to each other in said plane;
   b) monitoring the radiation emitted, scattered or absorbed by said particles as they traverse said slits;
   c) identifying specific said particles for which the entire particle traverses both said slits by identifying said particles for which the relative amount of radiation, emitted, scattered or absorbed at each slit as said particles sequentially traverse said slits bears a predetermined relationship dependent on the relative widths of said slits; and
   d) determining the size of said specific particles from the amount of said radiation emitted, scattered or absorbed as they traverse said slits.

2. A method as claimed in claim 1, wherein said slits are of equal width and different lengths, and said predetermined relationship is substantial equality.

3. A method as claimed in claim 2, wherein the emitted, scatter or absorbed radiation is continually monitored and the size of particles is determined from the radiation emitted, scattered or absorbed when a plurality of closely adjacent peaks corresponding to the number of slits and having approximately the same height are observed.

4. A method as claimed in claim 1, comprising at least two said slits, one said slit being shorter than the other.

5. A method as claimed in claim 1 wherein an image of said slits is formed on said mask, and the difference in lengths of the slits exceeds the diameter of the image of the largest particles to be measured.

6. A method as claimed in claim 5, wherein said mask is located on the end of an optic fiber leading to at least one photodetector.

7. A method as claimed in claim 5, wherein the particle diameter is determined from the emitted radiation in accordance with the formula:

$$P(\lambda,T)d(\lambda) = \frac{C_1 S}{\lambda^5} \frac{\epsilon}{e^{c_2/\lambda T} - 1} d(\lambda) \quad (1)$$

where $d(\lambda)$ is the wavelength range of detection centered on $\lambda$, $c_1$ and $c_2$ are universal radiation constants, $\epsilon$ is the emissivity and T the temperature of the particles.

8. A method as claimed in claim 6, wherein said emissivity of said particles is detected at two different wavelengths.

9. A method as claimed in claim 8, wherein said radiation is split into two spectrally separated beams by a dichroic mirror receiving radiation from said optic fiber, and said beams are passed through different bandpass filters to respective photodetectors.

10. A method as claimed in claim 1, wherein the particles are illuminated by an intense light source, and the size is determined from the amount of scattered light.

11. An apparatus for monitoring in-flight particles, comprising:
    a) a mask for location in a plane generally parallel to the direction of travel of the particles to be monitored, said mask defining at least two slits that are generally parallel, of different lengths, and lie in a direction having at least a component at right angles to said direction of travel, and said slits further having their ends laterally offset relative to each other in said plane;
    b) detector means for monitoring the radiation emitted, scattered or absorbed by said particles as they traverse said slits;
    c) means for identifying specific particles for which the entire particle traverses both said slits by identifying said particles that as they sequentially traverse each slit emit, scatter or absorb relative amounts of radiation in accordance with a predetermined relationship dependent on the relative widths of said slits; and
    d) processing means for calculating the size of the identified particles from the amount of said radiation emitted, scattered or absorbed by said particles.

12. An apparatus as claimed in claim 11, wherein said slits are of different length.

13. An apparatus as claimed in claim 12, wherein said slits have the same width.

14. An apparatus as claimed in claim 13, wherein the shorter slit is symmetrically disposed with respect to the longer slit.

15. An apparatus as claimed in claim 11, further comprising a lens for focusing an image of the particles onto said slits.

16. An apparatus as claimed in claim 14, wherein the difference in length of said slits is greater or equal to the diameter of the largest particles to monitored.

17. An apparatus as claimed in claim 11, wherein said detector means comprises two detectors for monitoring different wavelengths.

18. An apparatus as claimed in claim 17, further comprising a dichroic mirror for separately directing radiation from said slits to respective said detectors.

19. An apparatus as claimed in claim 13, wherein said identifying means monitors the radiation emitted, scattered or absorbed by the particles and identifies particles for which the amount is the same as they traverse adjacent slits.

20. An apparatus as claimed in claim 15, wherein said mask is located on the end of an optic fiber.

21. An apparatus as claimed in claim 11, wherein said processing means further calculates the temperature of said particles from the radiation emitted thereby.

22. An apparatus as claimed in claim 21, wherein said processing means calculates the velocity of said particles from the transit time between adjacent said slits.

* * * * *